United States Patent
Imboden et al.

(10) Patent No.: US 8,821,421 B2
(45) Date of Patent: Sep. 2, 2014

(54) MASSAGE DEVICE WITH FLEXIBLE SUBSTRUCTURE

(75) Inventors: Ethan F. Imboden, San Francisco, CA (US); Yves Behar, San Francisco, CA (US); Josh Morenstein, San Francisco, CA (US); Jeff Wyatt, Bozeman, MT (US)

(73) Assignee: JJ Acquisition, LLC, San Francisco, CA (US)

( * ) Notice: Subject to any disclaimer, the term of this patent is extended or adjusted under 35 U.S.C. 154(b) by 258 days.

(21) Appl. No.: 12/868,498

(22) Filed: Aug. 25, 2010

(65) Prior Publication Data

US 2011/0071445 A1    Mar. 24, 2011

Related U.S. Application Data

(60) Provisional application No. 61/237,186, filed on Aug. 26, 2009.

(51) Int. Cl.
*A61H 5/00* (2006.01)

(52) U.S. Cl.
USPC .............................. 601/46; 601/134; 601/135

(58) Field of Classification Search
USPC ................ 601/46, 72, 84, 134, 135, 137, 140
See application file for complete search history.

(56) References Cited

U.S. PATENT DOCUMENTS

| | | | |
|---|---|---|---|
| D85,323 S | 10/1931 | Carder | D26/104 |
| D197,889 S | 4/1964 | Hass | D24/194 |
| 3,364,922 A * | 1/1968 | Teranishi | 601/72 |
| 3,699,952 A | 10/1972 | Waters et al. | 601/18 |
| 4,149,530 A | 4/1979 | Gow | 601/72 |
| 4,878,489 A | 11/1989 | Kamayachi | 128/36 |
| 5,176,130 A | 1/1993 | Kim | 601/15 |
| D345,801 S | 4/1994 | Bosch | D24/200 |
| 5,336,159 A | 8/1994 | Cheng | 601/15 |
| 5,413,551 A | 5/1995 | Wu | 601/46 |
| 5,471,695 A * | 12/1995 | Aiyar | 15/22.1 |
| D366,673 S | 1/1996 | Harling-Berg | D21/623 |
| D366,703 S | 1/1996 | Huen | D24/214 |
| 5,704,902 A | 1/1998 | Vandenbelt et al. | 601/72 |

(Continued)

FOREIGN PATENT DOCUMENTS

AU    2004 200 676 A1    9/2004
DE    33 16 100 A1    11/1984

(Continued)

OTHER PUBLICATIONS

International Search Report and Written Opinion, Appl. No. PCT/US2010/046656, Apr. 29, 2011.

(Continued)

*Primary Examiner* — Michael A. Brown
(74) *Attorney, Agent, or Firm* — Ungaretti & Harris LLP

(57) ABSTRACT

A massage device, methods and apparatus are disclosed. Embodiments of a massage device are provided that include a first end configured to be held and manipulated by the hand of a user and a second end configured for application to a portion of the human body. The device further includes a flexible portion connecting the first end to the second end. The flexible portion contains a source of vibrational motion and has a rigidity of an amount sufficient to transmit the vibrational motion from the source to the second end of the device.

11 Claims, 10 Drawing Sheets

(56) References Cited

U.S. PATENT DOCUMENTS

| | | | |
|---|---|---|---|
| 5,857,986 A | 1/1999 | Moriyasu | 601/49 |
| 5,894,670 A | 4/1999 | Iso et al. | 30/541 |
| D414,582 S | 9/1999 | Hwang | D28/9 |
| 5,951,500 A | 9/1999 | Cutler | 601/47 |
| 5,956,484 A | 9/1999 | Rosenberg et al. | 709/203 |
| 5,966,821 A | 10/1999 | Armbruster et al. | 30/537 |
| 6,027,463 A | 2/2000 | Moriyasu | 601/46 |
| 6,028,531 A | 2/2000 | Wanderlich | 340/7.6 |
| 6,234,986 B1 | 5/2001 | Raffo et al. | 601/72 |
| 6,312,397 B1 | 11/2001 | Gebhard | 601/15 |
| D454,959 S | 3/2002 | Harris et al. | D24/215 |
| 6,368,268 B1 | 4/2002 | Sandvick et al. | 600/38 |
| 6,432,071 B1 | 8/2002 | Hsieh | 601/72 |
| D466,217 S | 11/2002 | Harris et al. | D24/215 |
| D466,612 S | 12/2002 | Harris et al. | D24/215 |
| D475,793 S | 6/2003 | Tinsley | D24/214 |
| D476,087 S | 6/2003 | Dirks et al. | D24/215 |
| D485,910 S | 1/2004 | Chan | D24/215 |
| 6,741,895 B1 | 5/2004 | Gafni et al. | 607/138 |
| D509,301 S | 9/2005 | Talbot et al. | D24/215 |
| D510,628 S | 10/2005 | Talbot et al. | D24/215 |
| D517,218 S | 3/2006 | Kalen | D24/215 |
| 7,026,789 B2 | 4/2006 | Bozzone et al. | 320/108 |
| D523,562 S | 6/2006 | Telford | D24/215 |
| 7,083,581 B2 | 8/2006 | Tsai | 601/15 |
| 7,169,120 B2 | 1/2007 | Murdock et al. | 601/129 |
| D539,917 S | 4/2007 | Park | D24/215 |
| D546,958 S | 7/2007 | Kim | D24/215 |
| D549,350 S | 8/2007 | Wu | D24/215 |
| 7,282,036 B2 | 10/2007 | Masuda | 601/72 |
| 7,282,037 B2 | 10/2007 | Cho | 601/80 |
| D571,926 S | 6/2008 | Wu | D24/215 |
| D574,504 S | 8/2008 | Imboden et al. | D24/215 |
| D576,739 S | 9/2008 | Mock et al. | D25/48 |
| D576,769 S | 9/2008 | McGarity | D28/73 |
| 7,438,681 B2 | 10/2008 | Kobashikawa et al. | 600/38 |
| D583,064 S | 12/2008 | Ferber et al. | D24/215 |
| D586,469 S | 2/2009 | Henry | D24/200 |
| D597,211 S | 7/2009 | Ewing et al. | D24/187 |
| 7,577,476 B2 | 8/2009 | Hochman et al. | 600/546 |
| D610,695 S | 2/2010 | Forte | D24/211 |
| D612,511 S | 3/2010 | Mills et al. | D24/212 |
| 7,733,056 B2 | 6/2010 | Hartung et al. | 320/114 |
| 7,749,178 B2 | 7/2010 | Imboden et al. | 601/15 |
| 7,815,582 B2 | 10/2010 | Imboden et al. | 601/15 |
| D631,972 S | 2/2011 | Imboden et al. | D24/215 |
| D631,973 S | 2/2011 | Imboden et al. | D24/215 |
| D631,974 S | 2/2011 | Imboden et al. | D24/215 |
| 7,938,789 B2 | 5/2011 | Imboden et al. | 601/46 |
| 7,946,977 B2 | 5/2011 | Klearman et al. | 600/38 |
| 2002/0065477 A1 | 5/2002 | Boyd et al. | 601/47 |
| 2002/0095103 A1 | 7/2002 | Blue | 601/46 |
| 2002/0133103 A1 | 9/2002 | Williams et al. | 601/46 |
| 2002/0156402 A1 | 10/2002 | Woog et al. | 601/46 |
| 2003/0103088 A1 | 6/2003 | Dresti et al. | 345/835 |
| 2003/0195441 A1 | 10/2003 | Firouzgar | 601/46 |
| 2004/0068213 A1 | 4/2004 | Fujisawa | 601/70 |
| 2004/0132439 A1 | 7/2004 | Tyagi et al. | 455/419 |
| 2004/0193079 A1 | 9/2004 | Siddhartha | 601/72 |
| 2004/0260212 A1 | 12/2004 | Cho | 601/15 |
| 2005/0004429 A1 | 1/2005 | Tracanna | 600/38 |
| 2005/0027794 A1 | 2/2005 | Decker | 709/201 |
| 2005/0054450 A1 | 3/2005 | Yamaguchi | 463/58 |
| 2005/0075072 A1 | 4/2005 | Apitzsch | 455/41.2 |
| 2005/0075589 A1* | 4/2005 | Friedland | 601/72 |
| 2005/0090768 A1 | 4/2005 | Brattesani et al. | 601/70 |
| 2005/0203448 A1 | 9/2005 | Harris, Jr. et al. | 601/72 |
| 2005/0268472 A1 | 12/2005 | Bourilkov et al. | 30/537 |
| 2006/0058714 A1 | 3/2006 | Rhoades | 601/73 |
| 2006/0278514 A1 | 12/2006 | Roussin-Bouchard | 200/512 |
| 2007/0055096 A1 | 3/2007 | Berry et al. | 600/38 |
| 2007/0179412 A1 | 8/2007 | Imboden et al. | 601/72 |
| 2007/0179413 A1 | 8/2007 | Imboden et al. | 601/72 |
| 2007/0179414 A1 | 8/2007 | Imboden et al. | 601/72 |
| 2008/0009775 A1 | 1/2008 | Murison | 601/46 |
| 2008/0091128 A1 | 4/2008 | Nan | 601/70 |
| 2008/0154161 A1 | 6/2008 | Abbott | 601/113 |
| 2008/0306417 A1 | 12/2008 | Imboden et al. | 601/134 |

FOREIGN PATENT DOCUMENTS

| | | |
|---|---|---|
| DE | 103 52 219 A1 | 6/2005 |
| DE | 20 2005 015 767 U1 | 2/2006 |
| JP | 2002-308355 A | 10/2002 |
| JP | 2003-070866 A | 3/2003 |
| JP | 2003-144508 A | 5/2003 |
| JP | 2005-007164 A | 1/2005 |
| JP | 2005-237911 A | 9/2005 |
| KR | 10-1990-0017556 A | 12/1990 |
| KR | 20-0336728 Y1 | 12/2003 |
| KR | 20-0345467 Y1 | 3/2004 |
| NL | 9300507 A | 10/1994 |
| WO | WO 99/37267 A1 | 7/1999 |
| WO | WO 01/08628 A1 | 2/2001 |
| WO | WO 2004/069128 A1 | 8/2004 |

OTHER PUBLICATIONS

International Search Report and Written Opinion, Appl. No. PCT/US2007/02259, Dec. 17, 2007.

Partial International Search Report, Appl. No. PCT/US2008/050641, Apr. 28, 2008.

International Search Report and Written Opinion, Appl. No. PCT/US2008/050641, Jun. 16, 2008.

Supplementary European Search Report, Appl. No. EP 10814279, Nov. 27, 2012.

Rocks-Off, Finger Tingles. http://www.rocks-off.us/finger_tingles.asp, Mar. 2009.

* cited by examiner

MASSAGE DEVICE WITH FLEXIBLE SUBSTRUCTURE

The present application claims the benefit of U.S. Provisional Patent Application No. 61/237,186 filed Aug. 26, 2009, which is incorporated herein in its entirety by reference.

SUMMARY

The present patent application relates to a massager, associated methods and apparatus. In some embodiments a massager is provided that includes a first end configured to be held and manipulated by the hand of a user and a second end configured for application to a portion of the human body. The massager further includes a flexible portion connecting the first end to the second end. The flexible portion contains a source of vibrational motion and has a rigidity of an amount sufficient to transmit the vibrational motion from the source to the second end of the device. In some embodiments, the flexible portion can extend into an interior of the second end of the device, thereby achieving the transmission of vibrational motion by positioning the source of vibrational motion within the second end of the device. Additionally or alternatively, the source of vibrational motion can extend beyond an end of the flexible portion and into the interior of the second end of the device. Further still, the source of vibrational motion can transmit the vibrational motion throughout the device.

According to various embodiments, a massager can comprise: a first end configured to be held and manipulated by the hand of a user; a second end configured for application to a portion of the human body; and a flexible portion connecting the first end to the second end, wherein the flexible portion contains a source of vibrational motion and has a rigidity of an amount sufficient to transmit the vibrational motion from the source to the second end of the device, wherein the source is disposed distal from the second end.

In some embodiments of the massager, the flexible portion comprises a flexible substructure and a boot covering the flexible substructure. In some embodiments, the flexible substructure has a Shore durometer value higher than a Shore durometer value of the boot. In one embodiment, the massager can include a valve to exchange air. The massager can be water-proof. The valve can comprise a membrane.

In some embodiments, the flexible portion can comprise two flexible members extending from the first end. One source can vibrate the two flexible members. In some embodiments, there can one be included one source per flexible member. Optionally, each source may be individually controllable. The massager can comprise a heat generating source.

In some embodiments, the vibrations from the source are dampened proximate the first end; the end for holding the massager. In some embodiments, the flexible portion is more flexible when bent on the Y-Z plane then when bent on the X-Y plane.

According to various embodiments, the massager can include a vibration source; a rib to define a shape, wherein the rib conducts vibrations from the vibration source; and a flexible material complimenting the rib. Stimulation may be applied through and with the flexible material to an area of the human body wherein the point of the contact to the human body is also a vibration point. The flexible material can include a flexible substructure and a boot covering the flexible substructure. The rib can define a shape adapted to receive a human digit.

According to various embodiments, a massager can include two flexible members extending from the device and having the tip of each members providing a point of vibration. The members can be manipulated to apply stimulation to the same point on the human body and can also be maneuvered to apply simultaneous stimulation in different points. The two members are approximately of the same height or dimension and are movable independently of one another. In some embodiments, each of the two flexible members comprises a flexible substructure and a boot covering the flexible substructure.

According to various embodiments, a massager may include a spine that configures the massager device to be more rigid in a first direction as opposed to a second direction. The spine may comprise a thin piece of material. The thin piece of material may have a rectangular shape.

The nature and various advantages of present inventive massager, methods, or apparatus will become more apparent upon consideration of the following description taken in conjunction with the accompanying drawings. Additional inventive systems, methods, process, or features can also be understood from the following description and drawings.

DETAILED DESCRIPTION

Figure 1:
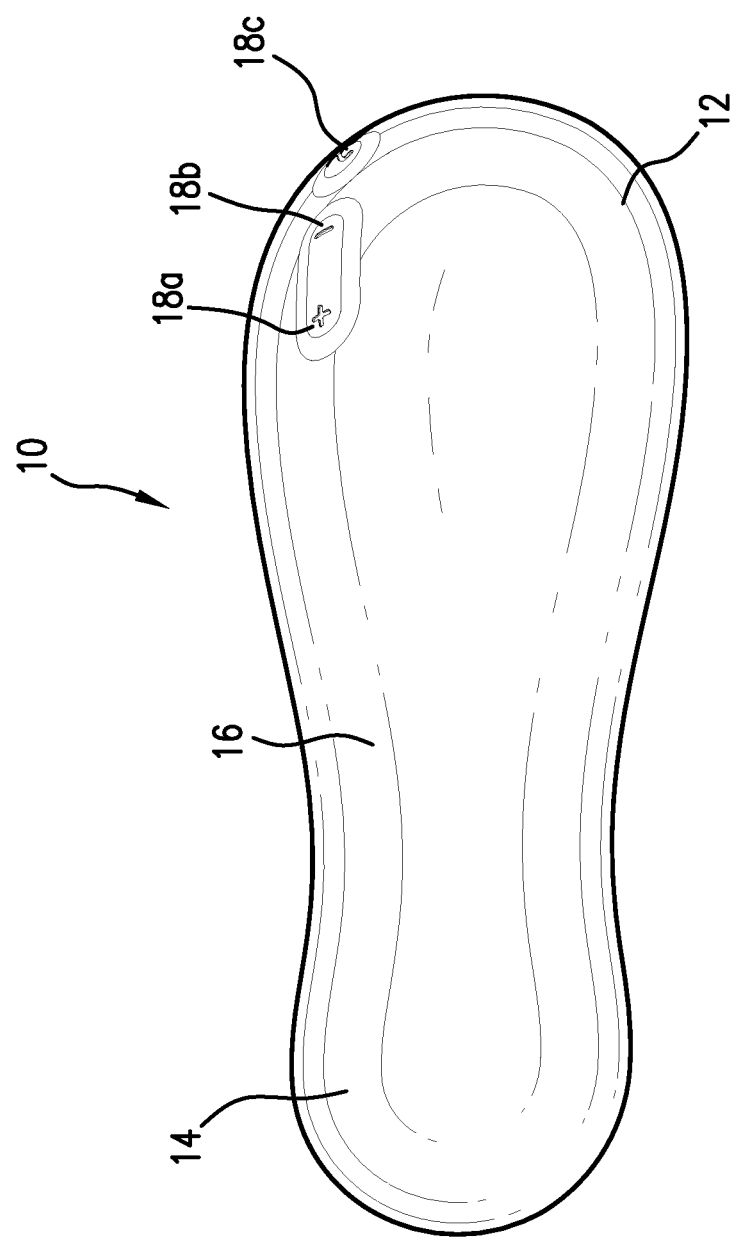
FIG. 1 is a front perspective view of a massager according to a first embodiment of the present invention.
Figure 2:
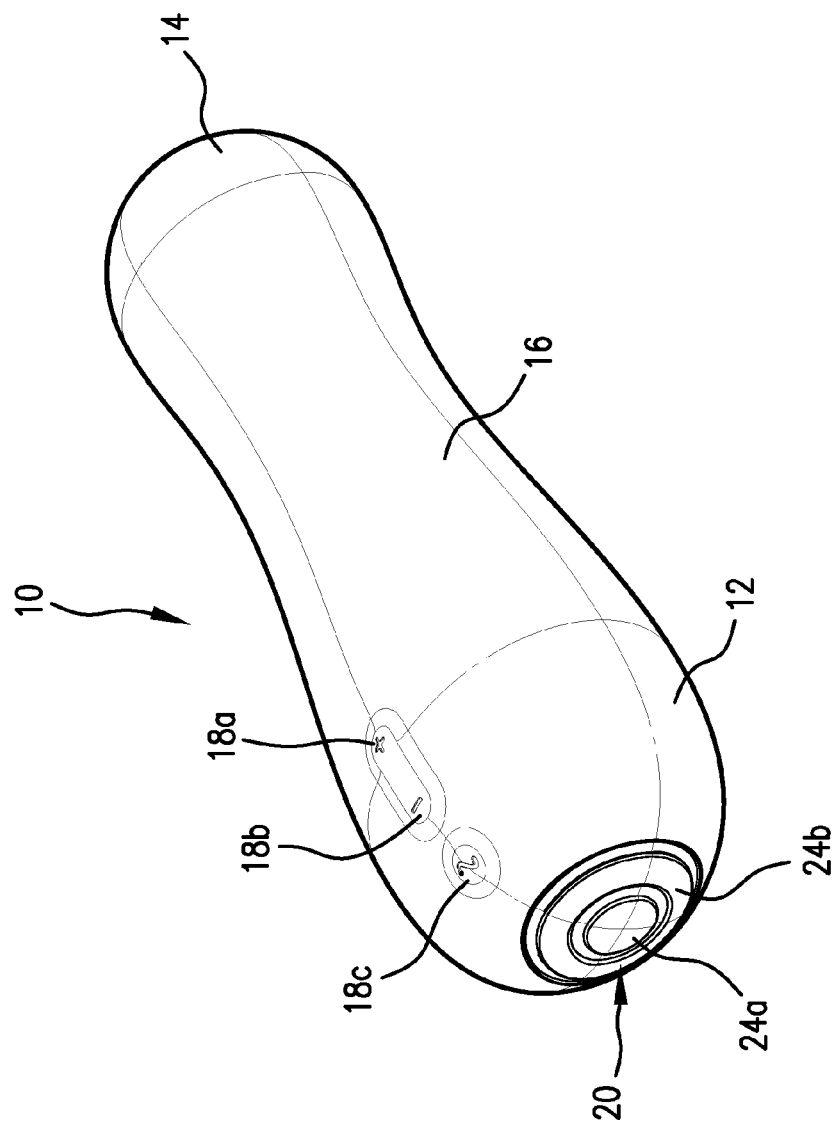
FIG. 2 is a rear perspective view of the massager of FIG. 1.

Turning to the drawing figures, where similar numbers are used to represent similar features, FIGS. 1 and 2 show an embodiment of the present invention, wherein a massager 10 includes a first end 12, a second end 14 and a midsection 16. In the present embodiment, first end 12 is in the form of a base end that includes controls for various electronic features of the massager 10 and also houses most of the electronic components of the massager 10, as discussed below with reference to FIG. 3. First end 12 is generally sized and shaped to provide a portion of the massager 10 for the user to grasp during use of the massager 10, but is also designed to provide a useable area for the massager 10. Accordingly, the majority of first end 10 is substantially smooth and forms a continuous, rounded surface, with the exception of the controls 18 and the charging contacts 20.

Second end 14 is generally intended to form the primary useable portion of massager 10 that is configured to be applied to various parts of the human body to achieve various forms of massage, including relaxation massage, muscular/tissue massage, and erotic massage. Regardless of the type of massage intended, it is desirable that second end 14 be shaped to provide a smooth surface that can comfortably move while in contact with the human body. It is also important that second end 14 be shaped to adequately direct the force applied by the user to the tissue upon which massager 10 is used, without creating discomfort through areas of excessive pressure.

Midsection 16 generally forms the transition or connection between first end 12 and second end 14. Depending on the specific form of the massager 10, midsection can take on a variety of specific shapes that may be largely dictated by the actual shapes of first and second ends 12, 14. Generally speaking, midsection 16 should be generally smooth throughout and should form substantially smooth transitions with and between first end 12 and second end 14. In various embodiments of the massager of the present invention, midsection 16 may contribute to aspects of the massage characteristics of the massager 10, as will be discussed below.

Figure 3:
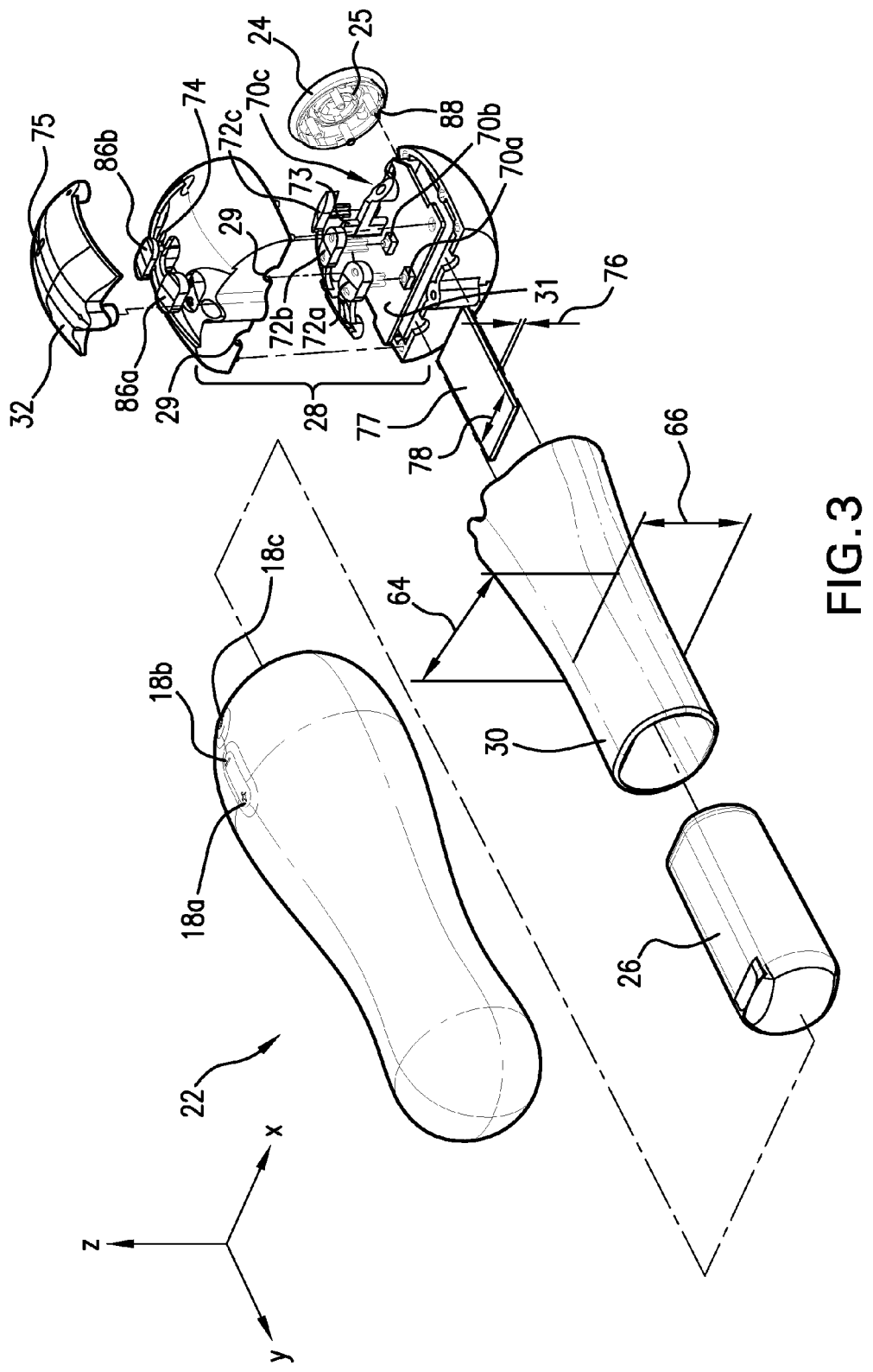
FIG. 3 is an exploded view of the massager of FIG. 1.

FIG. 3 is an exploded view of massager 10 that shows the structure of and relationship between both external and internal components of massager 10. Massager 10 includes an outer boot 22 that forms most of the outside surface of massager 10 and encloses its internal components. Preferably, the only portion of the outside surface of massager 10 that is not defined by boot 22 is the contact surfaces 24, which are used to make an electrical connection between massager 10 and a corresponding charging unit (discussed below) for purposes of recharging the massager 10 between uses. The internal components of massager include motor unit 26, control housing 28, and a flexible substructure 30. The internal components are assembled together and provide the structure for the overall shape of massager 10, with boot 10 being substantially flexible and compliant so as to provide a pleasant feel for the user and to smooth out the overall shape of massager 10.

Control housing 28 also encloses most of the electronic components of massager 10 such as a rechargeable battery and printed circuit board ("PCB"). The PCB 31 includes buttons that are used to control electronic functions of massager 10, such as turning on and off the electronic motor held within motor unit 26 as well as controlling the speed at which the motor rotates. Further control functions of the motor are disclosed in co-pending U.S. patent application Ser. No. 11/971,825 to Imboden, et al. (hereinafter, "the '825 Application") entitled "Rechargeable Personal Massager" and filed Jan. 1, 2008, the entire disclosure of which is incorporated by reference herein. The PCB 31 also controls the charging of the battery and, accordingly, is electronically connected to charging contacts 24a, 24b.

Figure 6:
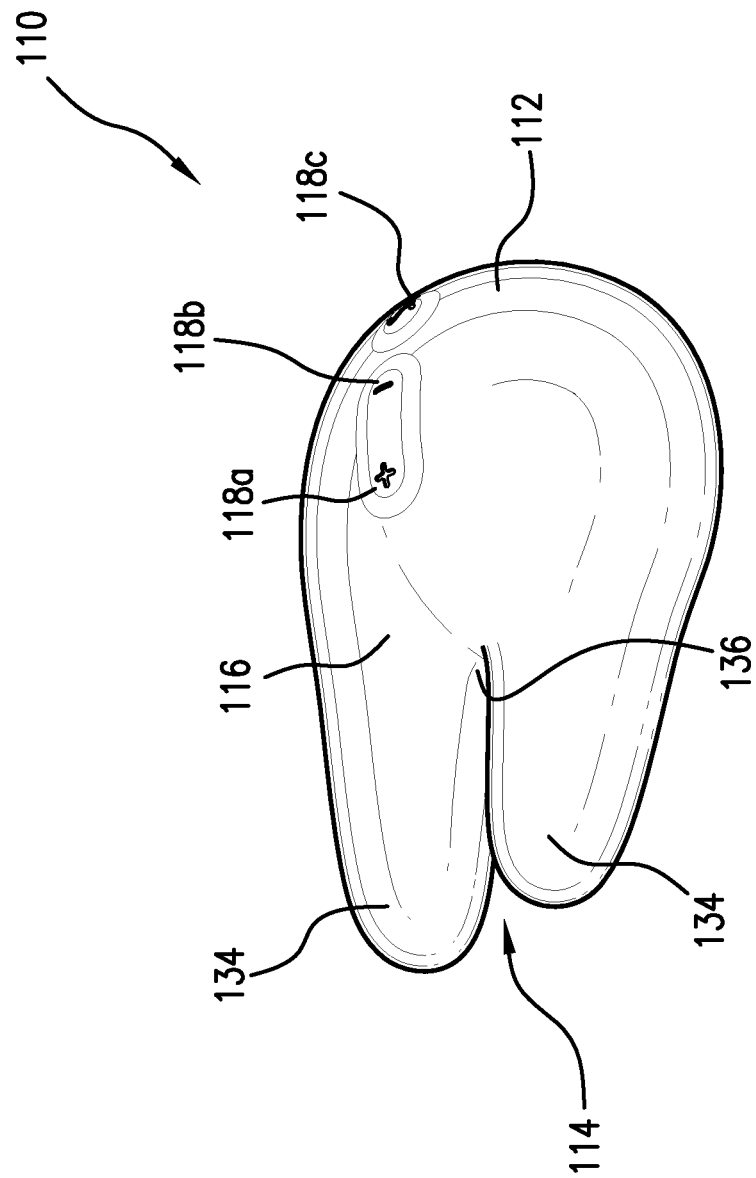
FIG. 6 is a front perspective view of a massager according to a second embodiment of the present invention.
Figure 7:
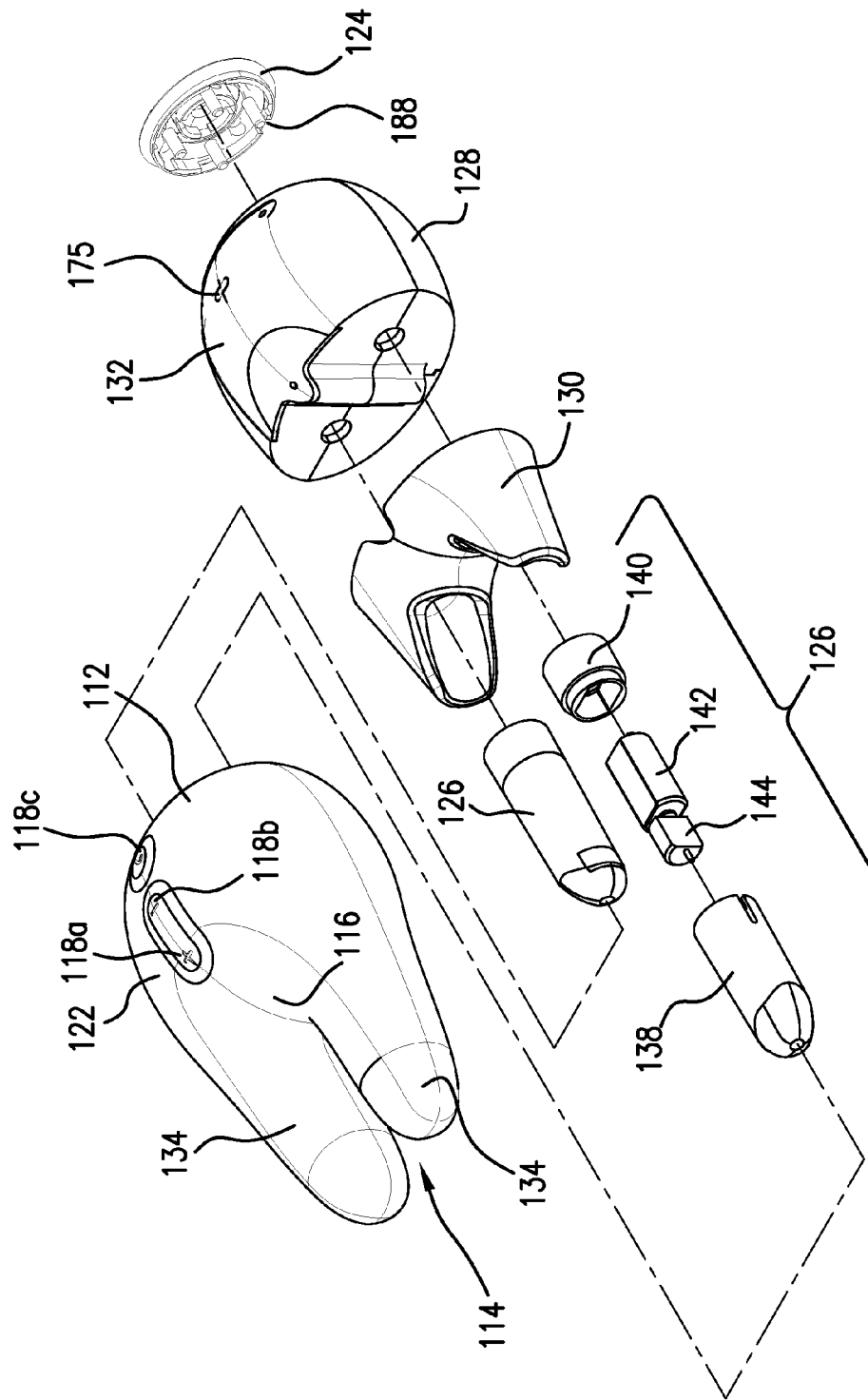
FIG. 7 is an exploded view of the massager of FIG. 6.
Figure 8:
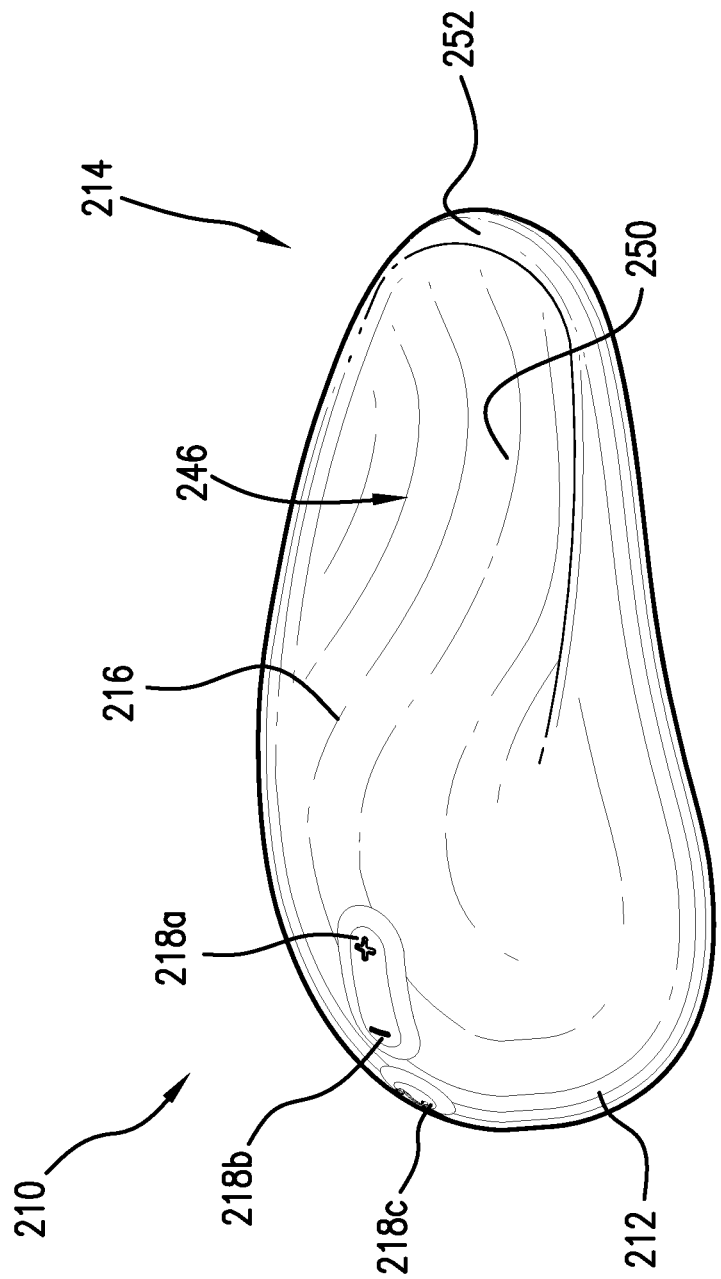
FIG. 8 is a front perspective view of a massager according to a third embodiment of the present invention.
Figure 9:
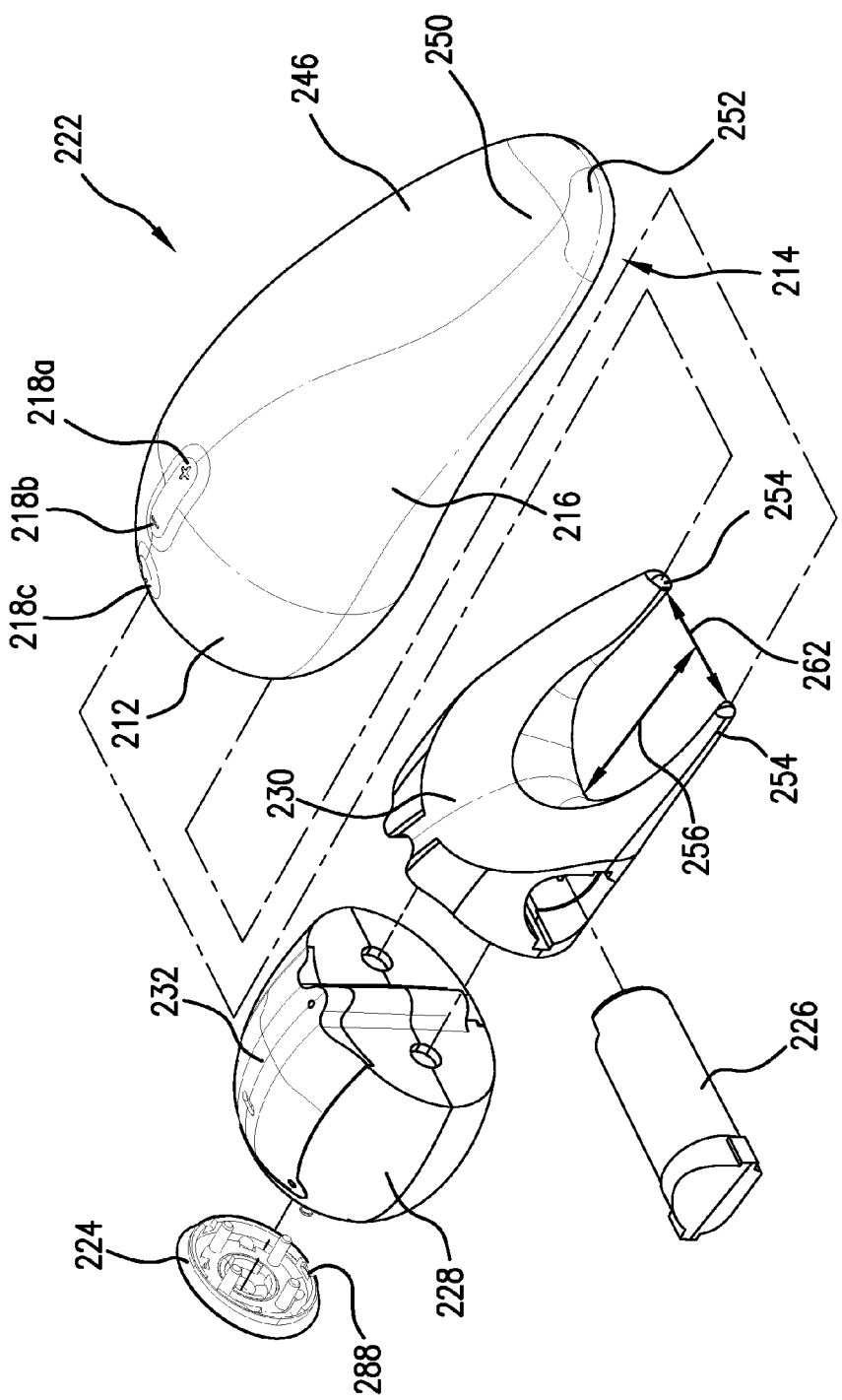
FIG. 9 is an exploded view of the massager of FIG. 7.
Figure 10:
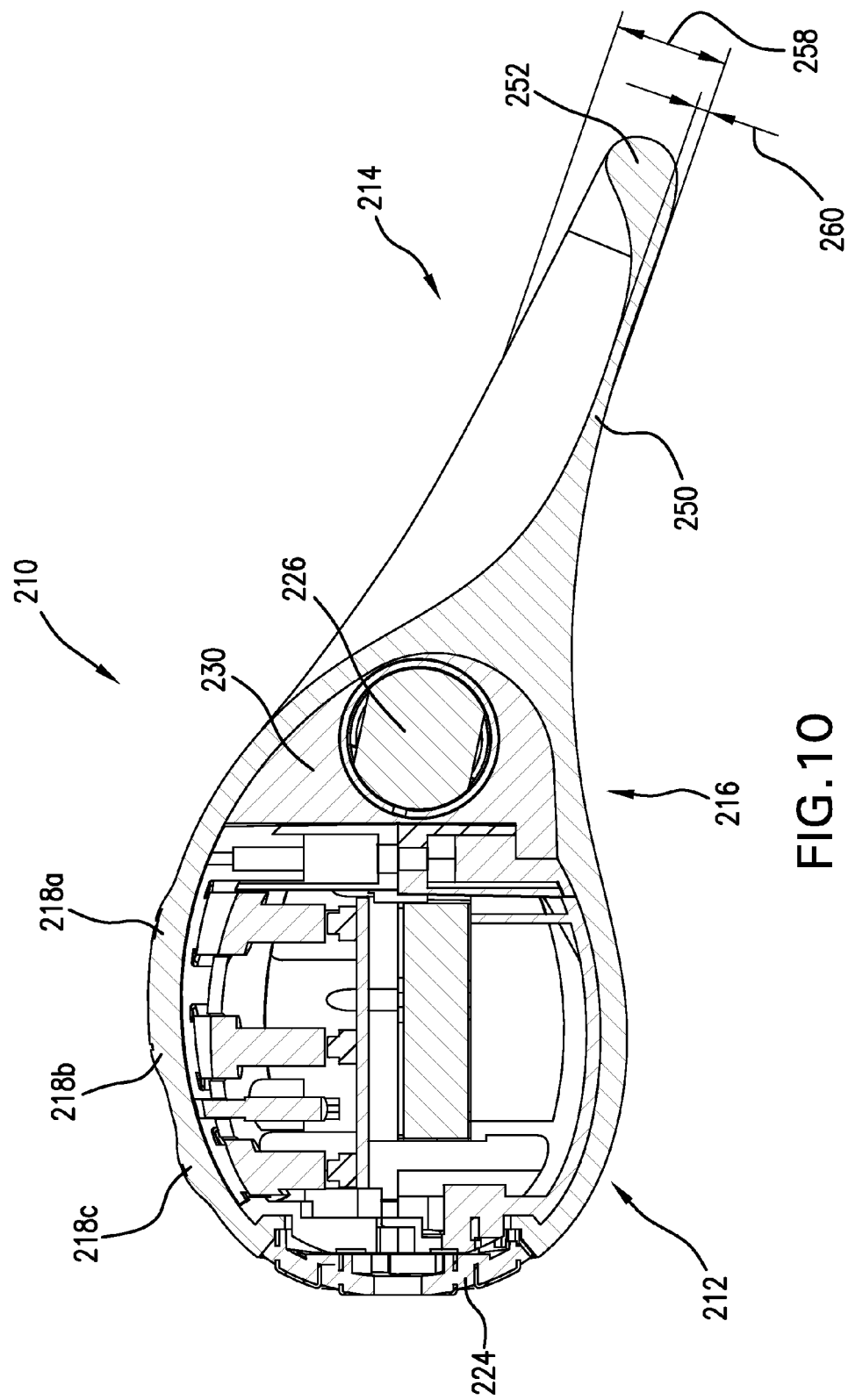
FIG. 10 is a cross-sectional view of the massager of FIG. 7.

In a preferred embodiment, control housing 28 is structured so as to be useable in a number of different massage devices that have varying shapes for their respective midsections and second ends. (See, for example massager 110, as shown in FIGS. 6 and 7, and massager 210, as shown in FIGS. 8-10.) In such an embodiment, control housing 28 can have a shape intended to be common to the first end 12 of the device with a feature for connection thereto of different flexible substructures. In the embodiment shown, control housing 28 includes a pair of holes 29 formed between mating halves of control housing 28 such that the two halves can be assembled to capture a mating portion of midsection 30 such as a pair of mushroom tabs (not shown) to secure flexible substructure 30 to control housing 28. Preferably, an adhesive can also be used to further secure the attachment. The PCB 31 included in control housing 28 can also be adapted to control common functions between various massager embodiments that share a common control housing. The PCB 31 can further be accessible during assembly of the device, such as by opening the housing to add additional elements to the PCB 31 to adapt the control features to the specific embodiment of the massager with which it is used. Such adaptations can include, for example, appropriate handling of the number and/or size of the vibrating motors used (which can result in varying power requirements) and can be achieved, for example, by soldering specific jumpers thereto, as would be understood by one of ordinary skill in the art. Variations of PCB 31 that are programmable or otherwise customizable to work with additional variations in massager types and configurations are contemplated. For example, PCB 31 can include flash memory or the like that can allow customization of massager control by changing firmware, rather than hardware.

The buttons 70a, 70b, 70c of PCB 31 are positioned beneath cover 32, which is substantially flexible such that when the user presses one of the controls 18a, 18b, 18c, cover 32 deforms therebeneath. Cover 32 is adaptable to provide a transition between a common control housing 28 and midsections of various configurations that may be used in a number of devices having different midsection and second end shapes. The use of cover 32, provides a smooth transition between control housing 28, and the flexible boot 22, especially during manipulation of controls 18a, 18b, 18c. Cover 32 further prevents any adhesives used during assembly of massager 10 from interfering with the functioning of controls 18a, 18b, 18c. Preferably, different covers can be used with corresponding flexible substructures wherein the different covers are configured to match the profile the portion of the control housing to which they connect and to vary along the remaining outside surface, according to the desired shape of the flexible substructure. This arrangement allows for a transition to the common control housing 28 from the various flexible substructure shapes to extend farther toward first end 12 than would otherwise be possible. Button tree 64 is positioned inside control housing 28 and is structured to depress a corresponding one of buttons 70a, 70b, 70c in response to the deformation of cover 32 when controls 18a, 18b, 18c are depressed. Specifically button tree 64 includes lever arms 72a, 72b, 72c that correspond to buttons 70a, 70b, 70c and provide a link through cover 32 to corresponding controls 18a, 18b, 18c. Preferably, the various forms of the cover that may be used in connection with the modular assembly structure described above are structured to maintain a similar "button feel" between different variations thereof. This button feel can include, for example, the force required to depress the controls and the distance of travel required for the manipulation of the controls to achieve their desired function. Consistent button feel can be achieved, for example, by forming the different variations of the cover to share a common thickness. Such a formation can result in a gap between the button tree and cover 32. In such instances spacers 86a, 86b can be included between buttons 70a, 70b, 70c and button tree 64 to take up this gap and to maintain a consistent travel distance for buttons 70a, 70b, 70c compared to other embodiments.

In the embodiment shown, there are three controls formed on boot 22, which include "+" control 18a (which increases motor speed), "−" control 18b (which decreases motor speed), and mode control 18c. Mode control 18c preferably cycles through various additional electronic functions or massage modes. Examples of these modes include: constant, sine curve slow, sine curve fast, ramping, and pulsing. These modes can additionally include control of multiple motors in embodiments of the massager including more than one motor. Examples of such modes are further described in the '825 Application. Controls 18a, 18b, 18c can also be used to activate a "secret mode" of operation for massager 10 by, for example pressing specific ones of controls 18a, 18b, 18c in a predetermined sequence. The secret mode can include the implementation of a certain vibrational characteristic for massager 10 or can include the implementation of a "chaos" mode, whereby the motor is made to vibrate in a random one of its prescribed modes at a random power level for a certain period of time before the mode is switched to another randomly-selected mode, and so forth. The secret mode or function can be one that is not described in the manual that is distributed with the device when it is sold. The sequence may involve pressing a combination of buttons to unlock the secret mode. For example, the existing functional buttons on the devices may not provide access to that function or mode and a code must be entered by using existing buttons to unlock and activate the mode. In some instances, such a function may not be necessarily considered to be a "secret" to the user, but there may be no corresponding button that is designated to activate the mode. Pressing a combination of different buttons, such as pressing "+" twice and "−" once within a few seconds, or by pressing the "+" and "−" controls within about ½ second of each other three times in sequence, for example, can trigger the mode. In other words, for example, the buttons for providing different functions on the massager are being used in an unconventional way (not having a known set function for their use in combination or not corresponding to their designated use) to cumulatively find a new operation of the massager, specifically a massager. In other embodiments, such "secret" functionality may be related to a game function of the massager. This can include using the geometry of the massager, in connection with the vibration of the motors to, for example, cause the massager to rotate on a surface for a random amount of time or through a random rotational distance. This allows the massager to be used to control a "spin-the-bottle" type game.

In an exemplary embodiment of a control scheme that can be used in connection with massager 10, the vibration level can be controlled by two methods:

1) by clicking the "+" control 18*a* or the "−" control 18*b* according to the following scheme:

Clicking "+" control 18*a* once increases the vibration level by one level

Clicking "−" control 18*b* decreases it by one level

Clicking "+" when massager 10 is on level 5 (the top speed) has no effect

Clicking "−" when massager 10 is on level 1 stops all vibration, turning massager 10 off; or, 2) by pressing and holding the "+" control 18*a* or "−" control 18*b* according to the following scheme:

Pressing and holding "+" control 18*a* causes the vibration level to step up through the levels, with 0.25 s between steps, until the button is released, or massager 10 reaches its top speed (LEVEL 5).

Pressing and holding "−" control 18*b* causes the vibration level to step down through the levels, with 0.25 s between steps, until the button is released, or massager 10 reaches level 1. (To then turn massager 10 all the way off, "−" control 18*b* must then either be held for an additional 0.5 s, or can be clicked or pressed again.)

In addition to the various controls of the vibration of massager 10 when the device is turned on, controls 18*a*, 18*b*, 18*c* can be used to turn massager 10 off and to enter a "lock" mode, preferably in accordance with the following exemplary scheme:

1) Behavior when massager 10 is "off":

Clicking or pressing and holding "−" control 18*b* or mode control 18*c* has no effect when massager 10 is off. (Clicking or pressing mode control 18*c* does not change the mode of vibration.)

Clicking "+" control 18*a* turns massager 10 on and begins vibration at level 1.

Pressing and holding "+" control 18*a* turns massager 10 on and begins vibration level 1 and continues to ramp up the speed until the button is released. Massager 10 will then continue to run at that speed When Vibrating Massager is turned on, the mode is always the same as when massager 10 was last turned off.

2) "Locking" and "unlocking" massager:

Pressing and holding "+" control 18*a* and mode control 18*c* simultaneously for 1.5 seconds locks and unlocks massager 10.

When massager 10 is on, and "+" control 18*a* and mode control 18*c* are pressed simultaneously for 1.5 seconds, the motor (or motors, if multiple motors are used) stops and massager 10 is locked.

When massager 10 is off, and the "+" control 18*a* and mode control 18*c* are pressed simultaneously for 1.5 seconds, the motor stays off and massager 10 is locked.

Whenever massager 10 is unlocked it will turn on and begin vibrating at level 1 and in the same mode it was in just prior to being locked.

Placing massager 10 in base 90 unlocks it and puts it in the off mode. Therefore massager 10 is always in the off mode (and not locked) when it is removed from base 90.

The control methods described are by way of example only and are not intended to be limiting with respect to the operation of massager 10. Different control schemes, employing more, fewer, or different controls can be implemented by those with ordinary skill in the art.

Control housing 28 further preferably includes an LED light assembly 73 that is comprised of a LED light source on PCB 31 and a light pipe that carries the light emitted by the LED light source to the end thereof. The light carried to the end of the light pipe of LED assembly 73 is visible through a hole 75 in cover 32 in control housing 28 and further visible through boot 22 due to the preferred material characteristics thereof. LED light assembly 73 can be used to provide information to the user of massager 10 regarding the status of the massager's operation. For example, LED light assembly 73 can indicate when the massager is on, off, or in locked mode by flashing or constantly illuminating according to a prescribed pattern. LED light assembly 73 can also provide information regarding the charge level of the battery, for example by illuminating for a predetermined amount of time or flashing a predetermined number of times when massager 10 is removed from its charging base 90. Additionally, a larger LED light assembly, a plurality of LED light assemblies, an electroluminescent panel, an OLED or other light source can be included in massager 10, possibly at varying locations throughout the interior of massager 110, such as beneath boot 22 on or near second end 114, so as to illuminate substantially the entire form of massager 10 or to illuminate a portion of massager 10 at one or more desired locations. Such "night light" or lighting functions could also include forming the internal components, where possible, from a translucent material and can be incorporated in the communicative aspects of LED light assembly 73, discussed above.

Boot 22 is preferably formed from a flexible, rubbery material such as a silicone or a thermoplastic elastomer ("TPE"). In a preferred embodiment, boot 22 is molded as a separate, unitary structure and is fitted over the assembled internal components of massager 10. The flexible nature of the silicone or TPE allows boot 22 to flex and stretch, as necessary, to fit over any larger portions of massager 10 during assembly. A flexible adhesive, such as a silicone-based adhesive is preferably applied between the internal components of massager 10 and the inside surface of boot 22 to maintain the appropriate position of boot 22. Preferably, a low-viscosity adhesive is applied to achieve a substantially thin and even layer of adhesive. The use of an adhesive to secure boot 22 to the internal components of massager 10 help to keep boot smooth and substantially free of bumps and wrinkles during use, particularly when massager is bent or flexed as allowed by flexible midsection 30. Further, the use of adhesive allows boot 22 to provide additional structural support for the internal components of massager 10 such as between motor housing 26 and flexible substructure 30 or between flexible substructure 30 and control housing 28. The material used to form boot 22 preferably has a durometer of between Shore 35 A and Shore 44 A, which provides a substantially soft and pliant tactile quality for boot 22 when formed at a preferred material thickness of between 1 mm to 10 mm and, more preferably, between 2 mm and 5 mm. It is noted that the preferred material thickness can vary with the desired material characteristics of boot 22, such as flexibility, softness, etc.

Boot 22 forms a flexible skin that preferably waterproofs the entire structure of massager 10, with the exception of the single boundary at its opening. This opening is substantially sealed by the adhesive between boot 22 and control housing 28 around the opening of boot. A portion of control housing 28 that is located within the opening of boot 28 is substantially waterproofed by using adhesive to seal any openings or seams therein, including the seam between halves of control housing 28 and the openings for the leads that connect the charging contacts 24a, 24b to the PCB 31 through control housing 28. Charging contact cap 20 fits into the opening in boot 22 and is affixed to control housing 28. Charging contact cap 20 is comprised of two metal contacts 24a, 24b that are insert-molded into a plastic structure. This production method (rather than assembly of separate parts) essentially fuses the parts together, making them a sealed, unified assembly. The assembly of charging contact cap 20 onto control housing 28, which is preferably achieved by a combination of pressure-fit and glue, captures a portion of boot 22 therebetween, providing pressure on boot 22, around its opening, to create a seal therebetween and to prevent boot 22 from pulling away from control housing 28 around the opening thereof or from charging contact cap 20 around the edge thereof. An O-ring or gasket, preferably formed from silicone is positioned within channel 25 formed in charging contact cap 24 between charging contacts 24a, 24b. Channel 25 is positioned to abut a portion of control housing 28 beneath charging contact cap 24, forming a seal therebetween, and, accordingly, isolating charging contacts 24a and 24b and their respective leads from each other. This arrangement helps to substantially prevent shorting between contacts 24a and 24b due to water that may enter beneath the outer portion of the charging contact, as defined by the channel 25. The result of this preferred combination of sealing measures preferably ensures a substantially waterproof seal, resulting in a completely-submersible massager 10. Additional waterproofing measures can be employed within massager 10, such as by forming joints between mating parts of control housing 28 with v-grooves that substantially accumulate glue therein when used to secure the parts together. The use of adhesive to secure boot 22 to the internal components of massager 10, as mentioned above, also helps to waterproof massager 10 by substantially sealing boot 22 over any seams in motor housing 26 or control housing 28.

In a preferred embodiment, it may be desired to allow ingress and egress of air from the inside of massager 10 to the outside to prevent separation of boot 22 from the internal components of massager 10 due to changes in air pressure caused by varying altitude or temperature. To provide for this ingress and egress, a selectively permeable membrane can be included in control housing 28. The selectively permeable membrane is preferably formed from Gore-Tex™ or other, similar materials that are constructed to allow permeation by air, but not by water or other liquids. Accordingly, this structure, acts as a valve for air movement, while retaining the desired waterproofing characteristics of massager 10. Adequate movement of air through such a valve can be achieved through an area as small as 3 mm$^2$ or less, and more preferably 1.5 mm$^2$ or less. The valve is preferably in the form of a Gore-Tex™ membrane that is secured by into an appropriately-sized section of plastic tubing, preferably by insert molding the tubing around the Gore-Tex™ membrane or by alternative methods such as adhesive, heat seating, ultrasonic welding or the like. In an alternative embodiment, a mechanical valve, such as a check-valve or the like can be used. The valve is then secured, preferably by glue or alternatively by ultrasonic welding or the like, into a corresponding hole in control housing. The valve hole is preferably positioned on control housing 28 so as to locate valve beneath charging contact cap 24 in the portion thereof that is outside of channel 25. A notch 88 is preferably formed in charging contact cap 20 to allow the air passing through the valve to escape therethrough to the outside of massager 10, or vice-versa.

Motor unit 26 contains an electronic motor with an output shaft having an offset weight attached thereto (see FIG. 7 detail and the description of the '825 Application) such that a vibration is created by the motor when running. The motor is electronically connected to the PCB 31, which controls and powers the motor via the battery, by wires that run through flexible substructure 30. In the embodiment shown motor unit 26 is positioned within second end 14 of massager 10. Although other arrangements are possible, the arrangement shown in FIG. 3 can be preferred, where the size and shape of second end 14 permits, because it achieves the maximum amount of transfer from the vibrating motor to the point of application for massager 10.

Flexible substructure 30 is formed to provide a level of compliance or flexion to the structure of massager 10. Depending on the overall form of the massager, it might be desired to have different portions thereof be compliant or flexible, but in the embodiment shown in FIGS. 1-3 it is desired to include flexibility between first end 12 and second end 14. The flexibility provided by flexible substructure 30 has many benefits, including making massager 10 more compatible with different portions of the human body or to compensate for variations within specific body parts between different individuals. Additionally, the flexibility can increase comfort and provide a more lifelike feel for massager 10. It can also allow the user to change, to an extent, the relative position of different portions of the massager, in this case first end 12 and second end 14, which can provide variations within the sensations provided by massager and/or allow the user to provide sensation to different body parts, simultaneously. In an additional embodiment, flexible substructure 30 (or flexible substructures 130 in FIGS. 6 and 7 and 230 in FIGS. 8-10) can be formed to have a certain amount of "memory", either by material selection or by including additional structures therein, such as pliable wire, hinges, spines, a flexible conduit or the like. Such additional structures would preferably be substantially covered by, or embedded in, the material of flexible substructure 30. For example, spine 77, as shown in FIG. 3, or a similar structure, can be formed from a material that is capable of being manipulated into a bent shape that it can substantially hold. Alternatively, spine 77 can be adapted to include a mechanical structure that can bend and hold a shape and can be further adapted to affix to motor housing 26 at one end and to control housing 28 at the other.

The use of such structures incorporating some degree of memory can allow the user of massager 10 (or massager 110 or massager 210) to direct the force applied by massager, and preferably by second end 14, to a specific part or parts of the body or can allow for second end 14 to reach to a specific part or parts of the body that otherwise might be more difficult to reach. Generally, the amount of memory provided will be such that the selected shape would not significantly change under the force of normal use, but can be changed or adjusted by the user, when desired. In some embodiments, the position can be selectively locked and unlocked by the user. Flexible substructure 30 also provides support for motor unit 26 within the massager 10, protects the wiring connections between motor unit 26 and control housing 28, and supports the outer boot 22 during flexion of massager 10 so that the skin formed by boot 22 is as smooth as possible before, during, and after flexion. Preferably, flexible substructure 30 is formed from IPE, or other flexible material such as silicone or the like, of a higher durometer than that used for boot 22. Depending on the desired characteristics of flexible substructure 30, the durometer of the TPE used can preferably fall within a range of 44 Shore A to 70 Shore A. Such characteristics, include the desired thickness, of both the substructure 30 and the portion of massager 10 in which it is used, the desired flexibility, the structural support of motor unit 26 and the amount of vibration transmission through flexible substructure 30 that is desired, among others. Additionally, the physical structure of the flexible substructure 30 can be tuned to provide the desired flexion/compliance characteristics. In a preferred embodiment, the thickness 64 of the cross-section of flexible substructure 30 in a X-direction is greater than the thickness 66 of the cross-section of the flexible substructure 30 in the Z-direction, as shown in the axes of FIG. 3. This results in the flexible substructure 30 being more flexible when bent on the Y-Z plane than when bent on the X-Y plane. Preferably, the ratio of thickness 66 to thickness 64 is less than 1 and, more preferably, less than about 0.75. In another example, the cross-section can be narrowed in specific areas to create a "hinge" in a specified area or tapered to vary the flexion along the length of the substructure. Ribs can also be integrally formed into the shape of the flexible substructure to change the flexion characteristics thereof, as desired. Additionally, the connections to adjacent or enclosed parts can be adjusted to change the flexion or compliance characteristics. For example, the distance to which motor unit 26 extends into flexible substructure 30 in the embodiment of FIGS. 1-3 can be changed to yield different characteristics for the assembled structure. If desired, a first and second direction different from horizontal and vertical direction mentioned above may be implemented (e.g., not in perpendicular orientation to each other).

Figure 4:
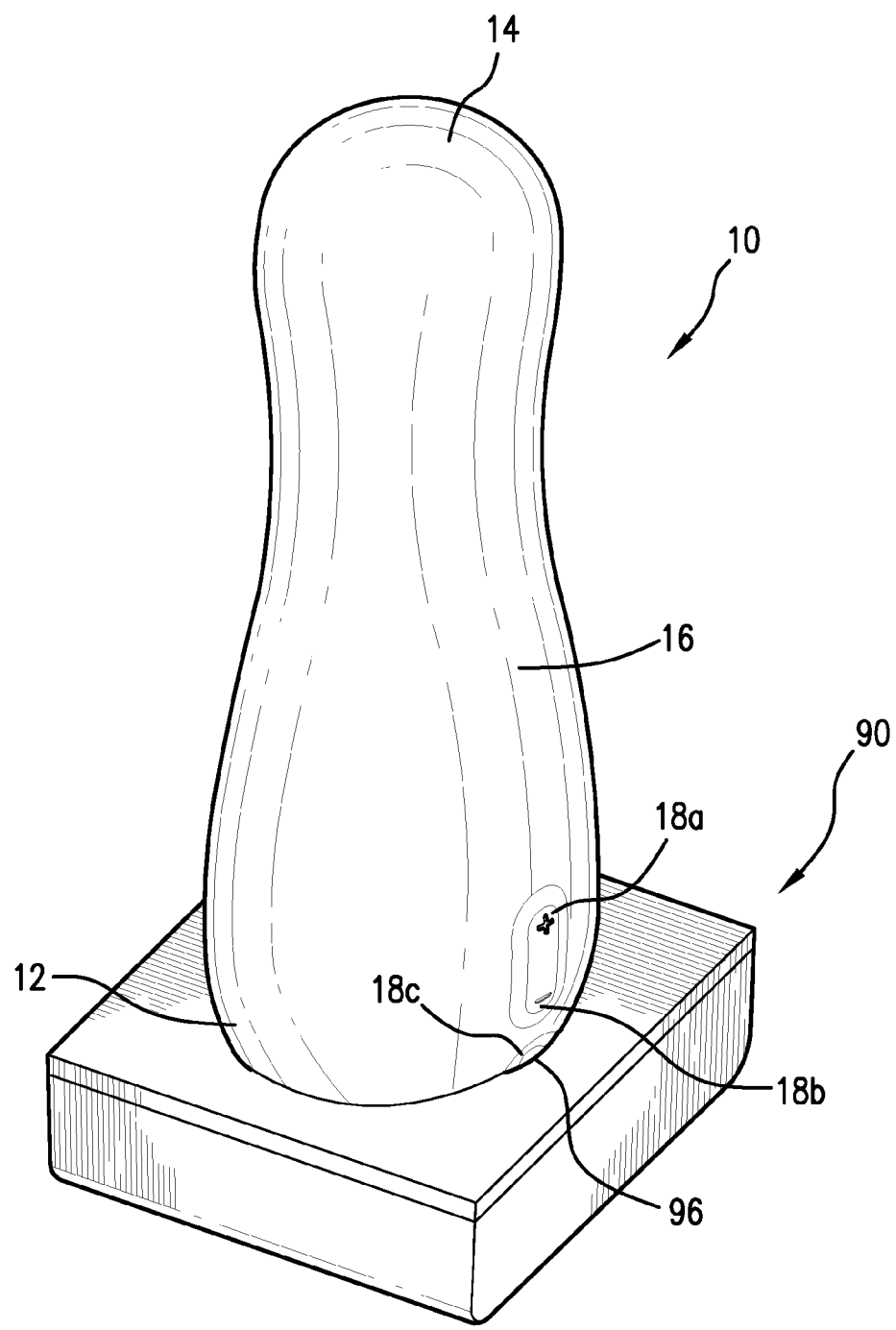
FIG. 4 is a perspective view of the massager of FIG. 1 assembled with a charging base.
Figure 5:
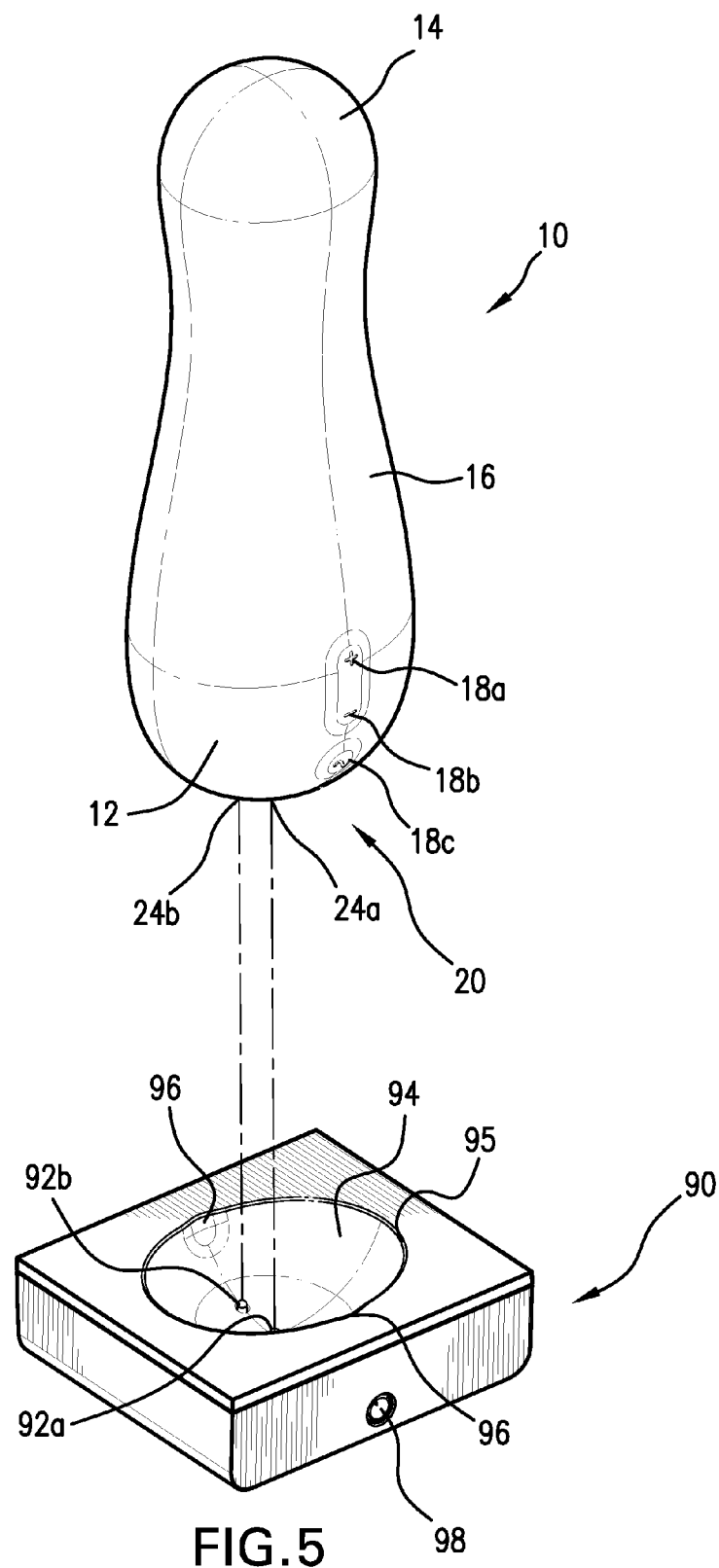
FIG. 5 is an exploded view of the assembly of FIG. 4.

In a preferred embodiment, a relatively thin piece of material can be included in flexible substructure by insert-molding, assembly using adhesives, or the like, to form a spine 77 that runs through a portion of the interior of flexible substructure 30. Preferably the thin piece of material that forms spine 77 is of a material, such as PET, that is, overall, less flexible than the material used for flexible substructure 30. This allows for the spine 77 to be flexible in the desired direction of flexion for substructure 30 (the direction on the Y-Z plane in the illustrated embodiment) by virtue of the low material thickness 76, but to also be relatively rigid in the other direction (the direction on the X-Y plane in the illustrated embodiment) due to the width 78 of the material. In such an embodiment, the ratio of thickness 66 to thickness 64 has a reduced effect on the flexion characteristics of flexible substructure 30 and is substantially free to vary according to other design aspects. The flexion characteristics of flexible substructure can be adjusted, as desired, by changing the configuration of spine 77, such as by altering the shape (e.g., tapering spine 77 along its length), or adjusting the thickness 76, its width 78 or the distance by which it extends into flexible substructure 30. Preferably, flexible substructure 30 and spine 77 are structured such that the ratio of the force required to achieve flexion in the direction on the Y-Z plane to the force required to achieve flexion in the direction on the X-Y plane is less than about 0.75 and more preferably about 0.5. FIGS. 4 and 5 show the use of an embodiment of a charging base 90 with an embodiment of a massager 10. Charging base has a pair of electrical contacts 92a, 92b that align with respective ones of the contacts 24a, 24b included in charging contact cap 20 to provide positive and negative connections to provide power to massager 10, preferably for recharging the battery contained within control housing 28. Charging base 90 is preferably formed so as to be as low as possible while still retaining massager 10 on base 90 so as to maintain electrical contact between charging contacts 24a, 24b, and contacts 92a,92b. In a preferred embodiment, as illustrated in FIGS. 4 and 5, base 90 is further structured to hold massager 10 in a substantially vertical arrangement, although other configurations are possible. As shown in FIGS. 6-9, the massager and base of the present invention can take various forms, including those beyond which are specifically shown herein. However, it is possible to construct a number of different massagers according to the general principles of the present invention that all work properly with a similar charging base, such as that shown in FIGS. 4 and 5. For example, all such massagers could have the same general shape for the portion of first end 12 that surrounds charging contact cap 20 (which could also be substantially similar between different massager variations). This portion would be that which fits within cavity 94 to provide the desired support for the massager 10. The various shapes of the different massagers can diverge after such a portion. The lower the height of the base 90, the more easily a smooth transition between the common and unique portions of the various massagers can be made. Having the massager 10 "standing" in a substantially vertical, or upright, position is generally intuitive and ergonomic for the user, that is, such an orientation makes it easy to pick up and put down the massager 10. Additionally, a base that has a low profile makes it easier to place the massager 10 into the charging position without requiring excessive accuracy. Preferably, base 90 is structured such that it its relatively wide in the horizontal (i.e. X-Y) plane so that it will not tip over, even when massager 10 is inadvertently placed in base 90 on an angle. Additionally, base 90 is preferably low enough such that controls 18a, 18b, 18c and LED light assembly 73 are substantially visible when massager 10 is on base 90, although a portion of control 18c may be not be visible. Other configurations for base 90 are contemplated, such as a configuration with no indentation surrounding contacts 92a, 92b, but rather strategically placed supports, preferably at least two, that provide support to key areas of massager. Such a configuration can allow for further variations among different forms of the massagers with which base 90 can be used.

As shown in FIG. 5, contacts 92a and 92b of base 90 and the contacts 24a and 24b of massager 10 are preferably formed to reduce the accuracy with which the massager 10 must be placed on base 90 in order to make a proper electrical connection therebetween. For example, in the embodiments shown, contacts 24a and 24b of massager 10 are in the form of concentric rings, and contacts 92a and 92b of base are in the form of pins, spaced radially within cavity 94 to align with one of the rings. This allows contact to be made regardless of the rotational orientation between massager 10 and base 90 along the long axis of the massager 10. Further, by making the contact rings 24a and 24b substantially wider than the pins 92a and 92b, the angle of placement at which appropriate contact can be made is increased.

Of course, by lowering the height of base 90, it is possible that the overall stability of the massager-base interface might be adversely affected. Several features can be implemented to overcome these effects. For example, it can be important to ensure that the surfaces of cavity 94 and the portion of first end 12 that fit therein substantially match around the upper edge 95 of cavity 94 to achieve an accurate fit therebetween. To allow for a proper fit between first end 12 of massager 10 and cavity 94 of base 90 despite variations in either surface, it is preferably to form cavity such that it diverges from the substantially matching fit with massager 10 at upper edge 95 to an offset distance of between 0.1 mm and 1 mm, and more preferably about 0.5 mm in the area surrounding contact 92a. Additionally, the surface of cavity 94 can be made of substantially smooth and polished polycarbonate (PC) or ABS plastic that will positively interact with the somewhat tacky surface of the soft silicone or TPE boot 22 to provide increased adhesion. A notch 96 can be formed near the upper edge of cavity 94 to provide clearance for control 18 of massager 10 and to "key" massager 10 in place on base 90. Further, while it may be desired to include a spring force on contacts 92a and 92b, to increase the compliance thereof when making contact with contacts 24a and 24b, it may further be desirable to make such a spring force tower in value no that they do not push massager 10 off of base 90. Power input 98 allows for the connection of charging base to a power source, such as an A/C outlet via a power adapter or the like.

In some embodiments, the vibration source can be disposed distal from the massage end of the massager. By placing the vibration source distal from the point intended to massage, the flexion movement of the massage end can be greater than when the vibration source is placed proximate the end to be held by a user. Furthermore, placing the vibration source distal from the massage end allows for shaping the massage end as desired. With no bulky vibration source near the massage end, the massage end can be shaped to complement various body orifices or surfaces without being limited by the size of the electronics or a vibration source.

While many of the features discussed above with respect to FIGS. 1-3 can be applied to other variations and embodiments of the massager of the present invention, there are some features that are substantially applicable to the embodiment shown therein. For example, there are certain ergonomic dimensions that are important to the shape of massager 10. Massager 10 has to be large enough overall for it to feel satisfying, both during massage, and in particular when used to provide sexual stimulation by insertion into the vagina, etc. It is also important, however, to make massager 10 not so large as to feel inappropriate to most users. Further, the length of midsection 16 preferably meets two criteria: that it is long enough so that second end 14 can extend about 2-3 inches into the vagina, particularly along the anterior side thereof in order to reach the "g-spot" while being easily held by first end 12; and, that it is short enough to be approachable (i.e., not daunting, overwhelming, or embarrassing) in appearance for a majority of users. Additionally, it is preferred that midsection 16 form a relatively narrow "waist" between first end 12 and second end 14 to create a varying diameter along the longitudinal axis of massager 10 so as to provide additional stimulation to the entrance of the vagina (or anus) as it stretches and relaxes the tissues during insertion and withdrawal therefrom. Preferably, midsection 16 tapers from a waist that is, at the most narrow point, at least about 7.5% more narrow than second end 14, and more preferably at least about 10% more narrow than second end 14. The relative widths used to calculate the percentage decrease from second end 14 to the most narrow point of midsection 16 can be taken along the cross-sectional width, length, or both width and length of the second end 14 and midsection 16. Preferably, such tapering occurs smoothly over a length that is not so long as to reduce the perceptibility of the change by the user, such as over a length of 60 mm or less. Alternatively the tapering can occur over a short distance in the form of a step or the like. Other possible arrangements for the surface of both second end 14 and midsection 16 can be used to provide similar stimulation, such as the use of ribs, bumps, various textures, multiple or repeating sections of tapering or widening, etc.

Turning to the embodiment of massager 110 shown in FIGS. 6 and 7, a variation of the massager includes a midsection 116 that splits to form a second end 114 having a plurality of projections 134. The embodiment of FIGS. 6 and 7 shows two substantially similar projections. If desired in other embodiments, further projections can be included and the projections can be of varying sizes and functions (such as providing for attachment to or stimulation of various body parts). Massager 110 is structured such that midsection 116 is flexible, allowing the user to move and adjust projections 134, as desired to provide different actions or sensations. For example, projections 134 can be compressed together so that the respective ends thereof touch so that they can be inserted together into a single cavity or pressed together to grip sensitive tissue, such as the clitoris. Further, it may also be preferable for projections 134 to be moveable apart from one another so that they can stimulate different adjacent areas, simultaneously, such as the clitoris and the entrance to the vagina, the vagina and the anus, the testicles, the anus and the perineum, etc. Such flexion is dictated by both the materials (such as flexible substructure 130, See FIG. 7) and by the size/shape of the features. For example, the valley 136 formed between projections 134 is preferably deep enough to permit such movement. It is also noted that the shape of flexible substructure 130 can vary from that which is shown in FIG. 7. In particular, flexible substructure may extend farther up along motor housings 126 and/or may terminate along a plane oriented substantially perpendicular to or up to about 45° to the long axis of motor housings 126, although other variations are possible. The ends of projections 134 are preferably sized to be small enough (and close enough together) so that they can both be applied to the clitoris simultaneously, either the top and bottom or the left and right sides thereof, depending on the orientation of massager 110. Preferably, projections 134 have a length between about 1 cm and 8 cm, although variations are contemplated in which longer or shorter projections would be desired. As shown in FIG. 7, massager 110 includes two motor units 126, each including a motor housing 138, an end cap 140, an electronic motor 142 and an offset weight 144. The functions of the motor units 126 is substantially the same as discussed above with respect to FIGS. 1-3. Each of the motor units is positioned within a respective projection 134 to provide individual vibration thereto. The motors can be controlled by the PCB 31 that is held within control housing 128 (as discussed above with respect to FIGS. 1-3). Further, in a preferred embodiment, the motors 142 can be made to vibrate at different speeds, providing a different sensation between projections 134 when used separately, or providing overlapping "beats" when used together. Examples of such operation, and the control thereof is discussed further in the '825 Application. In this embodiment, it is preferable that flexible substructure be flexible enough, through material selection and structure, that the individual motor units 126 can vibrate the projections 134 at the selected frequencies without being adversely affected by the operation of the other motor. In the present embodiment of massager 110, it may also be beneficial to incorporate the use of alternative or additional sources of vibrational motion such as piezoelectric devices, solenoids, memory alloy, or the like, within projections 134 to provide vibration. This would allow, for example, smaller-sized projections than that which can be used with the vibrating motors shown. In the embodiments shown, the projections 134 are shown having a substantially smooth surface. If desired, other implementations of the projections are contemplated, such as having a textured surface or the like. Other functional aspects and structures of massager 110, including the use and interaction with a charging base, such as base 90 shown in FIGS. 4 and 5) are preferably substantially similar to those discussed above with respect to the embodiments of FIGS. 1-5.

FIGS. 8 and 9 show a further embodiment of a massager 210 in which second end 214 has an indentation 246 formed therein, which forms a flexible membrane 250 surrounded by a relatively more-rigid rib 252. The incorporation of the membrane 250 allows for tactile sensation to be transmitted through massager 210 both from, for example, the fingers of the user on one side to a part of the user's (or another person's) body on the other side. This allows the holder of the device to both provide their own, unique sensation to the point of application and to receive tactile feedback from the anatomy of the point of application. The rib 252 compliments the membrane 250 by maintaining the structure and general shape of second end 214, while preferably allowing some degree of and transmitting vibration from the motor unit 226 to the point of application. As shown in FIG. 9, flexible substructure 230 is formed having extensions 254 that surround a portion of membrane 250, which is formed substantially entirely within boot 222, and give the preferred support and vibration transmission to membrane 250. The physical structure as well as the material characteristics of flexible substructure 230 can be adjusted to achieve the desired flexibility and transmission. For example, flexible substructure 230 is preferably formed from a TPE having a durometer in the range between about 50 Shore A to about 70 Shore A. The length of the extensions 254 can also be adjusted to achieve the desired qualities of these characteristics. In a preferred embodiment, extensions 254 have a length 256 of between about 1 cm and 6 cm, and more preferably about 3.5 mm. These dimensions preferably represent an extension equal to between about 70% and 100% along the sides of the membrane 250. Additionally, it may be preferable to form flexible substructure 230 such that extensions are spaced apart at a distance 262 from each other of between about 15 mm and 120 mm and more preferably about 25 mm. Other embodiments of the massager are contemplated in which extensions 254 are curved inward toward each other to further encircle membrane 250 or in which extensions 254 meet each other at the ends thereof, completely encircling membrane 250.

Preferably, the structure of flexible substructure 230, including extensions 254, along with the shape of boot 222, including rib 252, result in a membrane 250 having a size of at least about 10 mm, measured at approximately the longest point, by at least about 10 mm, measured at approximately the widest point. Such a size is approximately the lowest that would be reasonable useful in an embodiment designed to transmit the force applied to membrane 250 by a single finger of a user, with no included room to accommodate finger motion over membrane 250. Alternatively, a structure is contemplated in which membrane 250 is adequately sized to be used with all four fingers of a user with included room for movement of the fingers within membrane 250. In such an embodiment, membrane can measure up to approximately 120 mm by 120 mm. In a preferred embodiment, membrane 250 is about 35 mm long, measured at approximately its longest point, by about 25 mm wide, measured at approximately the widest point. Second end 214 of massager 210 preferably has as thin a profile as possible, while still maintaining the desired structural and vibrational aspects of the massager. In a preferred embodiment, second end has a thickness 258 (shown in FIG. 10) between about 4 mm and 15 mm, but can vary depending on the type of material used and the size of membrane 250. Such a thin profile preferably allows massager, and in particular second end 214 to fit comfortably between two people during sexual intercourse, including when in the "missionary position", to provide targeted sexual stimulation. Further, the shape of first end 212 and the transition between first end 212 and midsection 216 is preferably shaped to fit comfortably within and beneath a woman's or man's hand so that it is cupped in the palm and the fingers naturally rest along its length, extending into contact with the membrane 250 such that manipulation thereof can be achieved using the fingers. The thinning of the material that comprises boot 222 is preferably adjusted to make membrane as pliable as possible when used as such, without compromising the structural integrity of membrane 250 and while maintaining enough rigidity to transmit vibration therethrough. In a preferred embodiment, membrane 250 has a thickness 260 of between about 0.5 mm in and 5 mm, depending on the desired size of membrane 250, the durometer of the material comprising membrane, the desired flexibility of membrane 250 and the durability requirements for massager 210. In some embodiments having a low durability requirement, thickness 260 can be as low as 0.25 mm. In a preferred embodiment, of massager 210, having a membrane size of approximately 25 mm by 35 mm, and being constructed of material having a durometer of between 35 Shore A to 44 Shore A, thickness 260 is preferably between about 0.5 mm and 2 mm, and more preferably about 1 mm.

Additionally, further embodiments are contemplated that include embedding sources of vibration, such as piezoelectric devices within membrane or embedding other objects, such as a small steel ball or the like, within membrane 250. Such features, when embedded in membrane, can improve vibration of membrane 250, vibration transmission from the fingers of the user to membrane 250 and the parts of the body to which massager 10 is applied, or the ease of deformation of membrane 250 by the user. Further, such embodiments may allow for different membrane characteristics, such as thicker or thinner material. Textural features can be added to the bottom surface of membrane 250 (i.e., the surface applied to the body), such as slits that expand into ribs when membrane 250 is stretched, bumps, ridges, or the like. Membrane 250 could be substantially open, with no rib 252, on one end, such as near the tip of massager 210, or could have an opening at its center, such as for a finger, a user's penis, or another device, such as a non-vibrating form (i.e., a dildo) or another vibrator, to pass through. Other forms of a massager are contemplated that incorporate a flexible membrane. For example, a membrane of a flexible material could be supported by a rigid frame, with or without a soft or pliable covering and/or be included with a device that substantially lacks a midsection or first end. In one example embodiment, the flexible material may be held by a supporting frame, wherein the supporting frame is not covered by a soft pliable covering.

Other functional aspects and structures of massager 210, including the use and interaction with a charging base, such as base 90 shown in FIGS. 4 and 5) are preferably substantially similar to those discussed above with respect to the embodiments of FIGS. 1-5.

The system is intended such that base 90 is adaptable to receive mating ends of various devices having different structures than those shown. Additional structures can be designed and added to new products. If desired contactless, or wireless, charging devices, such as inductive charging, may be used. The charging end may, if desired be substantially smooth and may include a soft overlying layer where the charging contacts are otherwise shown as exposed.

If desired, the massager device may be adapted to use a remote control. Examples of such incorporation are disclosed in the '825 Application as well as in co-pending U.S. patent application Ser. No. 11/344,987 to Imboden, et al.; Ser. No. 11/245,456 to Imboden, et al.; and Ser. No. 11/345,455 to Imboden, et al., the entire disclosures of which are incorporated herein.

If desired, the massager device may further be implemented in an embodiment that uses standard (i.e., non-rechargeable) batteries. In such an embodiment, charging contact cap 20 could, for example, be replaced by a cap over a cavity for receiving a battery or plurality of batteries. Further embodiments are contemplated in which the entire device or portions of it, such as the second end of the massager are not covered by a soft elastomer, but rather, for example, structures in which the working surface is constructed from plastic. Additionally, many aspects of the invention discussed above can be incorporated into other structures that are currently or may later be used for massage devices and/or to provide sexual stimulation. Additionally, the charger can be self-aligning and can be curved so as to be adapted to receive the massager.

The technology described herein may be applicable to other areas as well. While the inventions have been shown and described with respect to particular embodiments, it is not thus limited. Numerous modifications, changes and enhancements will now be apparent to the reader. A number of inventions are contemplated including those appended below in the illustrative claims below.

What is claimed is:

1. A massager, comprising:
a first end configured to be held and manipulated by the hand of a user;
a second end configured for application to a portion of the human body, the second end comprising at least two flexible members extending away from the first end and having the tip of each member providing a point of vibration by way of a source of vibrational motion that is disposed within the second end and distal from the tips, wherein the members can be manipulated to apply stimulation to the same point on the human body and can also be maneuvered to apply simultaneous stimulation in different points; and
a flexible portion connecting the first end to the second end, wherein the flexible portion comprises a flexible substructure and wherein the flexible substructure further comprises a boot and the flexible substructure has a Shore durometer value higher than a Shore durometer value of the boot.

2. A massager, comprising:
a first end configured to be held and manipulated by the hand of a user;
a second end configured for application to a portion of the human body, the second end comprising at least two flexible members extending away from the first end and having the tip of each member providing a point of vibration by way of a source of vibrational motion that is disposed within the second end and distal from the tips, wherein the members can be manipulated to apply stimulation to the same point on the human body and can also be maneuvered to apply simultaneous stimulation in different points;
a flexible portion connecting the first end to the second end; and
a valve to exchange air, wherein the first end, the second end, and the flexible portion comprise a water-proof body.

3. The massager of claim 2, wherein the flexible portion comprises a flexible substructure.

4. The massager of claim 2, wherein the valve comprises a membrane.

5. A massager, comprising:
a first end configured to be held and manipulated by the hand of a user;
a second end configured for application to a portion of the human body, the second end comprising at least two flexible members extending away from the first end and having the tip of each member providing a point of vibration by way of a source of vibrational motion that is disposed within the second end and distal from the tips, wherein the members can be manipulated to apply stimulation to the same point on the human body and can also be maneuvered to apply simultaneous stimulation in different points; and
a flexible portion connecting the first end to the second end, wherein the flexible portion comprises a flexible substructure and
wherein the flexible portion comprises a boot covering the flexible substructure.

6. The massager of claim 5, wherein the source is one source which vibrates the at least two flexible members.

7. The massager of claim 5, wherein the source comprises at least two sources, each source disposed in one of the flexible members.

8. The massager of claim 5, wherein the source comprises at least flexible members.

9. The massager of claim 5, further comprising a heat generating source.

10. The massager of claim 5, wherein the vibrations from the source are dampened proximate the first end.

11. The massager of claim 5, wherein the flexible portion is more flexible when bent on the Y-Z plane than when bent on the X-Y plane.

* * * * *

UNITED STATES PATENT AND TRADEMARK OFFICE
CERTIFICATE OF CORRECTION

PATENT NO.         : 8,821,421 B2
APPLICATION NO.    : 12/868498
DATED              : September 2, 2014
INVENTOR(S)        : Ethan F. Imboden et al.

It is certified that error appears in the above-identified patent and that said Letters Patent is hereby corrected as shown below:

In the Claims:

At Column 16, line 17, in Claim 2, delete "and" and insert --and,-- therefor;

At Column 16, lines 48-49, in Claim 8, delete "wherein the source comprises at least" and insert --further comprising a valley between the-- therefor.

Signed and Sealed this
Sixteenth Day of December, 2014

Michelle K. Lee
*Deputy Director of the United States Patent and Trademark Office*